US00PP20213P3

(12) United States Plant Patent
Fontanazza

(10) Patent No.: US PP20,213 P3
(45) Date of Patent: Aug. 11, 2009

(54) OLIVE TREE NAMED 'GIULIA'

(50) Latin Name: *Olea europaea*
Varietal Denomination: Giulia

(75) Inventor: Giuseppe Fontanazza, Perugia (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 67 days.

(21) Appl. No.: 11/643,663

(22) Filed: Dec. 22, 2006

(65) Prior Publication Data

US 2007/0150988 P1 Jun. 28, 2007

(30) Foreign Application Priority Data

Dec. 28, 2005 (IT) ..... RM2005NV000012

(51) Int. Cl.
*A01H 5/00* (2006.01)

(52) U.S. Cl. ..... Plt./158
(58) Field of Classification Search ..... Plt./158
See application file for complete search history.

(56) References Cited

U.S. PATENT DOCUMENTS

PP13,077 P2 * 10/2002 Fontanazza ..... Plt./158
2007/0150988 P1 * 6/2007 Fontanazza ..... Plt./158

OTHER PUBLICATIONS

UPOV ROM GTITM Computer Database, GTI Jouve Retrieval Software May 2005 Citations for 'Giulia'.*

* cited by examiner

*Primary Examiner*—Annette H Para
(74) *Attorney, Agent, or Firm*—Foley & Lardner LLP

(57) ABSTRACT

A new and distinct *Olea europaea L.* olive tree variety named, 'GIULIA', particularly characterized by moderately weak plant vigor; average branch spread; greyed-green bark color (RHS 191A); dark green foliage color (upper side, RHS 193A; lower side, RHS 195C); yellow-green opened flower color (RHS 150D); greyed-green flower bud color (RHS 145C); grey-brown seed (endocarp) color (RHS 199D); dark violet fruit (RHS 83A); self-pollinating variety; adaptation for high altitude rooting (low temperature tolerance) and high density plantations; an early production stage with a medium time of ripening; full mechanical harvesting; and high productivity and high oil yield.

5 Drawing Sheets

Latin name of the genus and species of the plant claimed: *Olea europaea.*
Variety denomination: 'GIULIA'.

BACKGROUND OF THE INVENTION

The present invention relates to a new and distinct variety of olive tree, botanically known as *Olea europaea L.* of the Oleaceae family, and hereinafter referred to by the variety denomination 'GIULIA'.

Olive oil continues to increase in popularity. Accordingly, there is a continuing need to develop new and improved olive oils to meet the increased demand for use in various food types and in cooking. Many olive varieties are self-sterile. As a result, there is a need for the development of new olive varieties which are self-pollinating and produce a high yield of new and improved olive oil for commercialization.

In order to meet these needs, the present invention is directed to a new *Olea* variety named 'GIULIA'. The new *Olea* variety 'GIULIA' is a product of a controlled breeding program conducted by the inventor, Giuseppe Fontanazza, over the last twenty-five (25) years in the different climatic olive growing regions of Garda, Umbria and Molise, Italy. The objective of the breeding program was to develop a new *Olea* variety which expressed self-pollinating properties and was adapted for high altitude rooting (low temperature tolerance), high density plantations, an early production stage with a medium time of ripening, full mechanical harvesting, high productivity and high oil yield.

The controlled breeding program which led to the discovery and selection of the new *Olea* variety 'GIULIA', was conducted by the inventor, Giuseppe Fontanazza, in Perugia Italy, over the last 25 years and included 2 separate periods. The first, lasting 15 years and ending in 1995, focused on identifying potential, promising Olea progeny to study further; and the second, beginning in 1995, focused on asexually reproducing and trial testing a single, *Olea* variety selected from the potential, promising *Olea* progeny. Thus, the new *Olea* variety 'GIULIA' was first discovered and selected by the inventor, Giuseppe Fontanazza in 1995 from the progeny produced by means of mass selection, deriving from the embryos obtained by free-pollination of a large seed population of the *Olea europaea L.* variety designated 'MORAIOLO' (unpatented) growing in a cultivated area in Perugia, Italy. The new *Olea* variety 'GIULIA' was selected by the inventor based on the plant being self-pollinating and adapted high altitude rooting (low temperature tolerance), high density plantations, an early production stage with a medium time of ripening, full mechanical harvesting, high productivity and high oil yield.

Asexual reproduction of the new *Olea* variety 'GIULIA' by self-rooting of a vegetative cutting was first performed in May 1997 in Garda (a lake region of Northern Italy where the climate on the coasts of this lake is mild), and in April 1995 in Umbria and in May 1998 in Molise (two regions of Central Italy). Asexual reproduction of the new *Olea* variety 'GIULIA' has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'GIULIA' which in combination distinguish this olive tree as a new and distinct variety:

1. moderately weak plant vigor;
2. average branch spread;
3. greyed-green bark color (RHS 191A);
4. dark green foliage color (upper side, RHS 193A; lower side, RHS 195C);
5. yellow-green opened flower color (RHS 150D);
6. greyed-green flower bud color (RHS 145C);
7. grey-brown seed (endocarp) color (RHS 199D);
8. dark violet fruit (RHS 83A);
9. self-pollinating variety;
10. adaptation for high altitude rooting (low temperature tolerance) and high density plantations;
11. an early production stage with a medium time of ripening;
12. full mechanical harvesting; and
13. high productivity and high oil yield.

In comparison to the parental variety, 'MORAIOLO' (unpatented), 'GIULIA' differs primarily in the traits listed in Table 1.

TABLE 1

| Trait | New Variety 'GIULIA' | Parental Cultivar 'MORAIOLO' (unpatented) |
|---|---|---|
| Pollinating Type | Self pollinating | Cross pollinating |
| Productivity | Early production and high productivity | Medium late productivity and lower productivity |
| Fruit Size | Medium size | Small size |
| Plantation Adaptation | Adapted for high density plantation | Not adapted for high density plantation |

Of the many commercial varieties known to the present inventor, the most similar in comparison to the new *Olea* variety 'GIULIA' are the *Olea* varieties 'FS-17' (upatented, but registered as FAVOLOSA®, U.S. Registration No. 2,826,893) and 'DON CARLO' (patented, U.S. Plant Pat. No. No. 13,077) in the following characteristics described in Table 2:

TABLE 2

| Trait | New Variety 'GIULIA' | Comparison Variety 1 'FS 17' (unpatented) | Comparison Variety 2 'DON CARLO' (patented) |
|---|---|---|---|
| Timing of Variety Ripening | Medium | Early | Late |
| Plantation Adaptation | High Density | High Density | High Density |

BRIEF DESCRIPTION OF THE DRAWINGS

The accompanying photographs illustrate the overall appearance of the new *Olea* variety 'GIULIA' showing the colors as true as is reasonably possible with colored reproductions of this type. Colors in the photographs may differ slightly from the color values cited in the detailed botanical description, which accurately describe the color of 'GIULIA'.

DETAILED BOTANICAL DESCRIPTION

Figure 1:
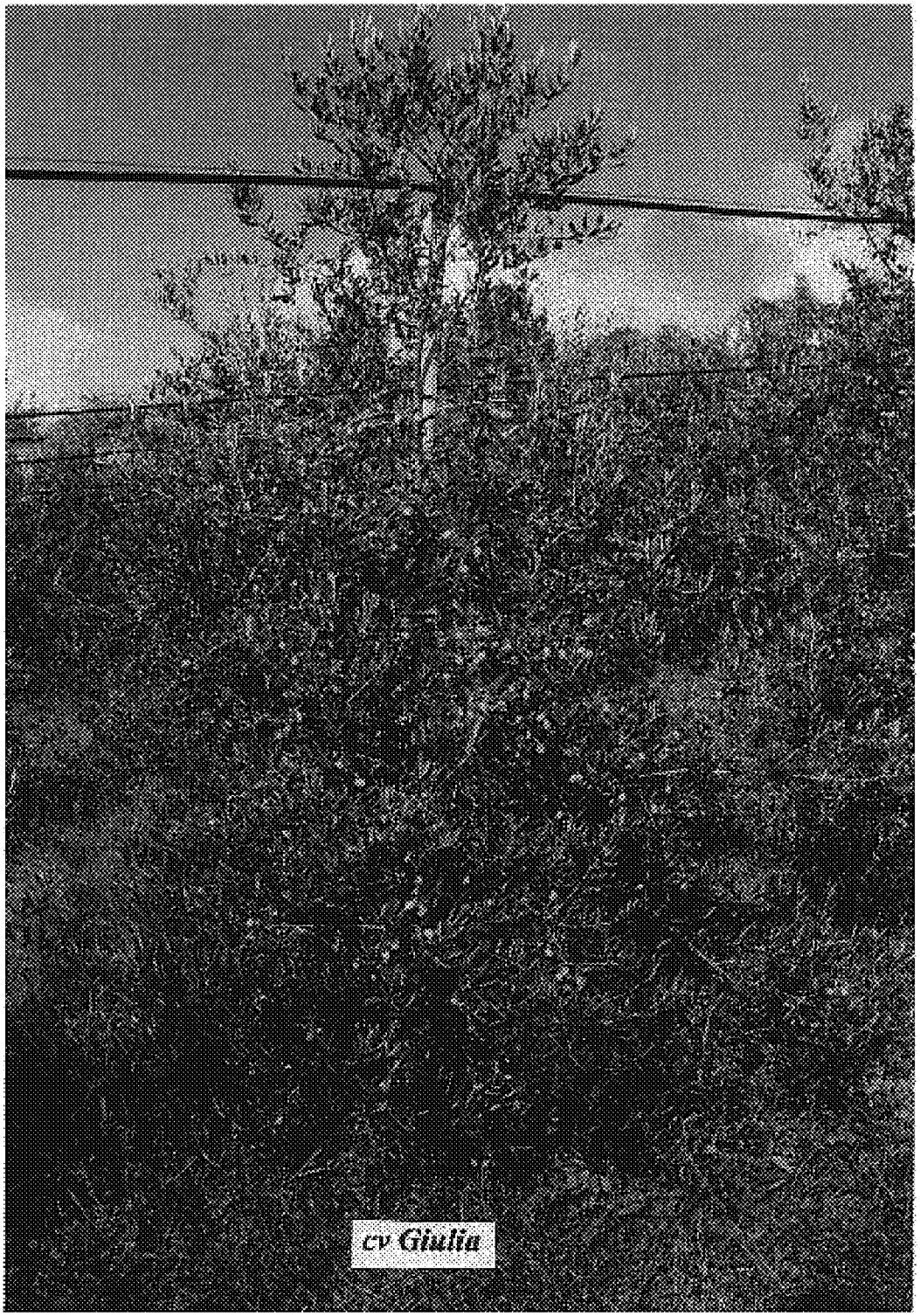
FIG. 1 is a photograph of a specimen of the new *Olea* variety 'GIULIA' exhibiting its overall appearance.
Figure 2:
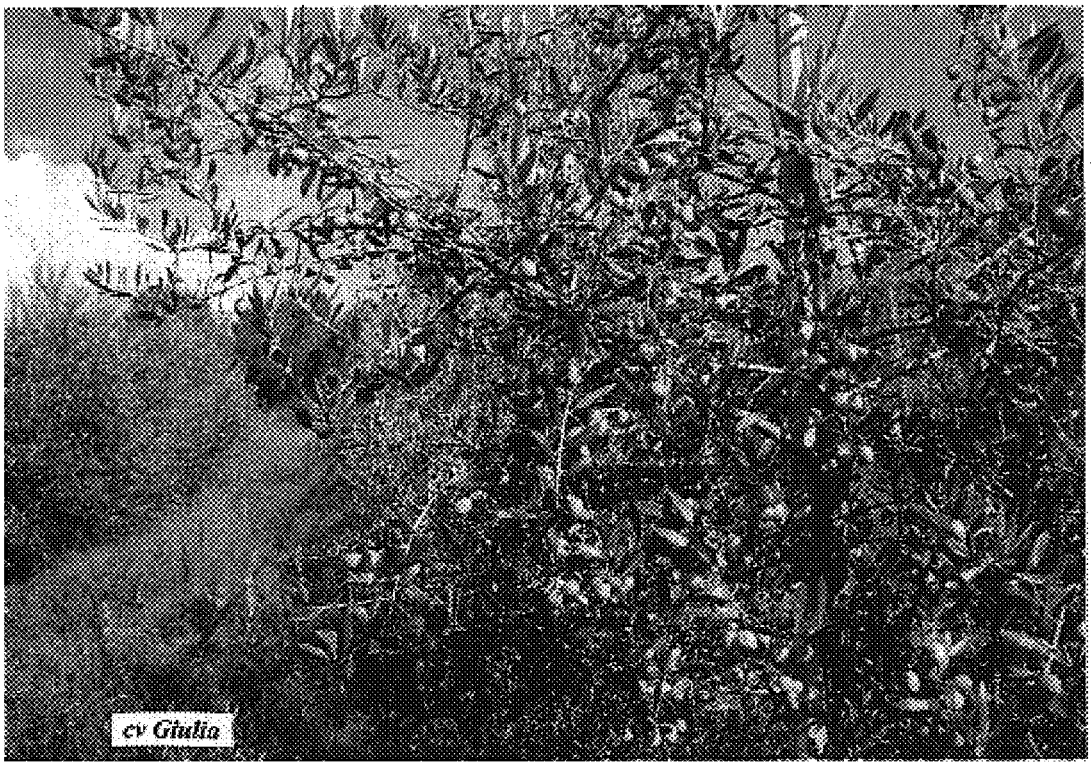
FIG. 2 and FIG. 3 are photographs of typical branches of the new *Olea* variety 'GIULIA' bearing fruit.
Figure 3:
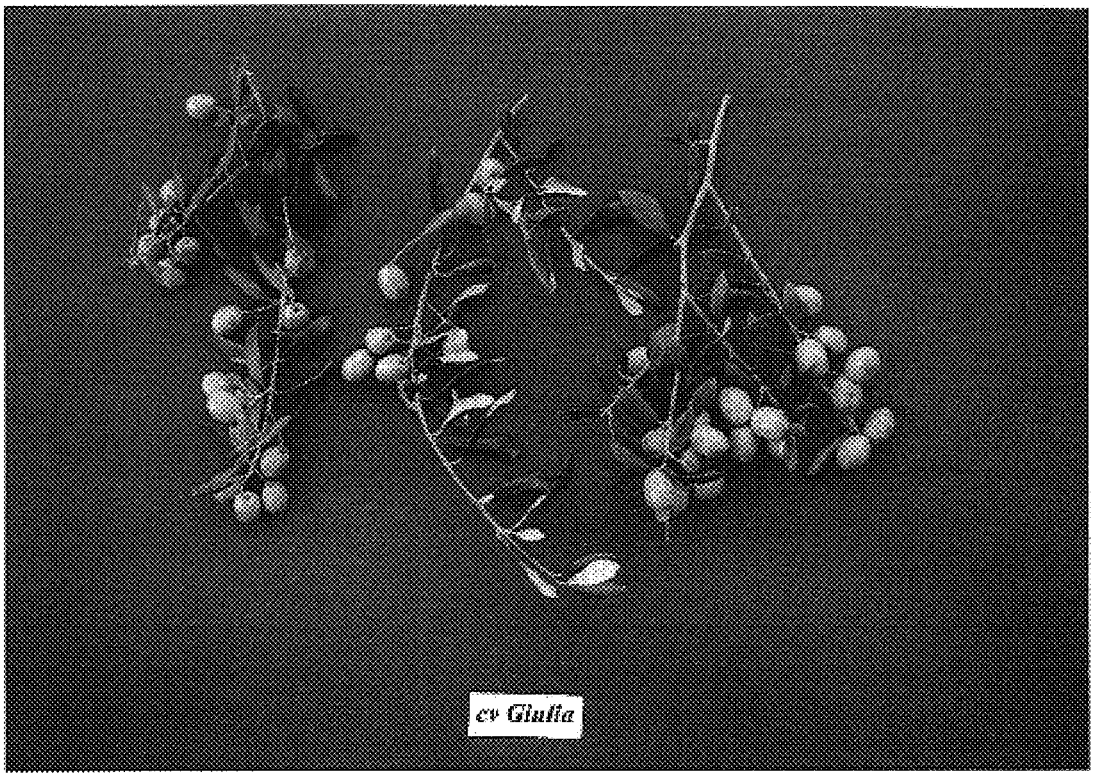
Figure 4:
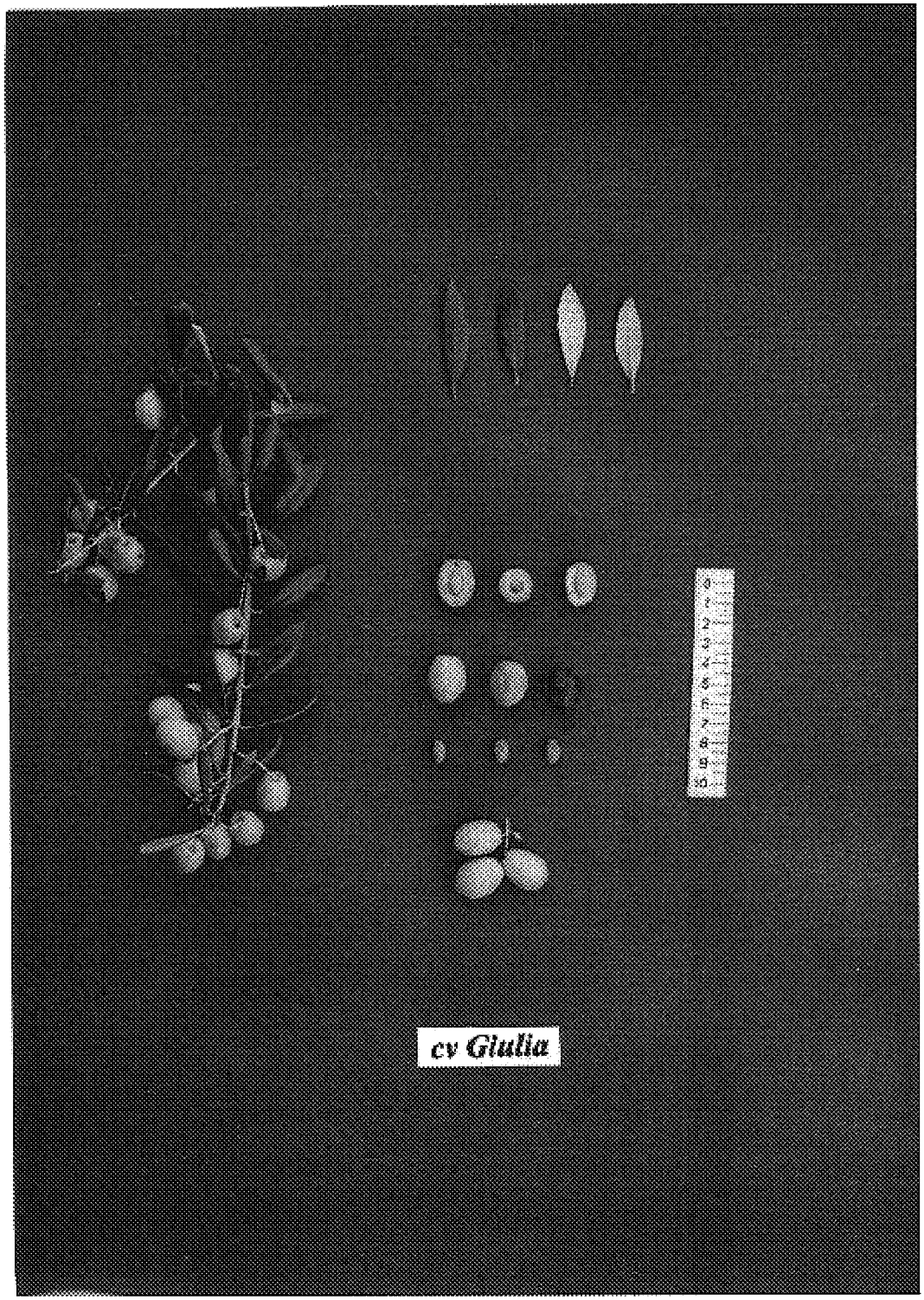
FIG. 4 is a photograph of a typical branch, the leaves (showing the upper side (two left leaves) and lower side (two right leaves), the fruit, a cross section of the fruit, and the seeds of the new *Olea* variety 'GIULIA'.
Figure 5:
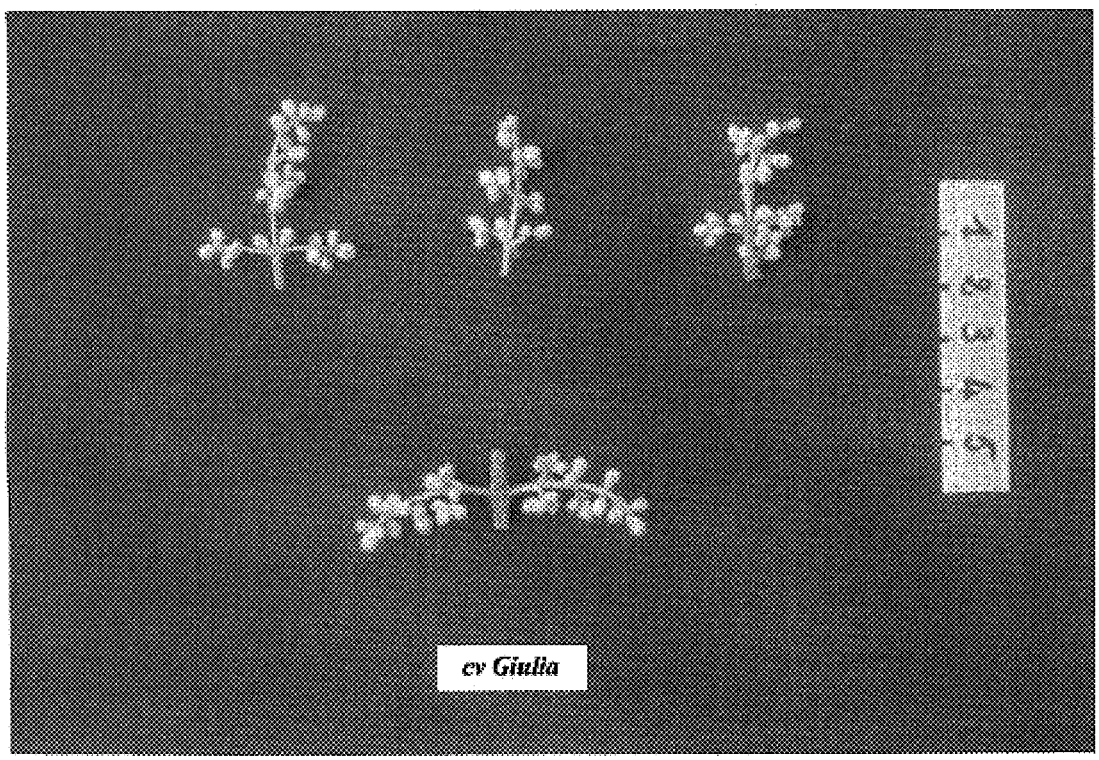
FIG. 5 is a photograph of the inflorescences of the new *Olea* variety 'GIULIA'.

The new *Olea* variety 'GIULIA' has not been observed under all possible environmental conditions. The phenotype of the new variety may vary with variations in environment such as temperature, light intensity, and day length without any change in the genotype of the olive tree.

The aforementioned photographs, together with the following observations, measurements and values describe trees of 'GIULIA' as grown over a period of about ten (10) years in different climatic environments of the olive farms in Garda, Umbria and Molise, Italy, under conditions which closely approximate those generally used in commercial practice. The new *Olea* variety 'GIULIA' grows well under both nursery and field conditions. The new *Olea* variety 'GIULIA' are grown with or without irrigation arranged by 5'×3' spacing, if rainfall is not less than 550–600 mm per year, with occasional rainfall in late spring and summer. After the third year of growth, the new variety 'GIULIA' forms very few sterile branches and the new growth shows reproductive properties. Accordingly, on the basis of the ten (10) year growing trials, the new *Olea* variety 'GIULIA' possesses excellent agronomic, biological and technological characteristics, which makes this new *Olea* variety of great commercial value.

Unless otherwise stated, the detailed botanical description includes observations, measurements and values based on ten (10) year old 'GIULIA' trees grown in olive farms located in Garda, Umbria and Molise, Italy, from 1995 to 2005. Quantified measurements are expressed as an average of measurements taken from a number of trees of 'GIULIA'. The measurements of any individual tree, or any group of trees, of the new variety may vary from the stated average.

Color references are made to the Royal Horticultural Society Colour Chart, original edition, except where general colors of ordinary significance are used. Color values were taken under daylight conditions at approximately 3:00 p.m. in Perugia, Italy.

All of the trees of 'GIULIA', insofar as they have been observed, have been identical in all the characteristics described below.

Classification:

*Botanical.*—*Olea europaea.*

Parentage: *Olea europaea L.* variety designated 'MORAIOLO' (unpatented).

Propagation: Self-rooting of a vegetative cutting.

Growth conditions:

*Light intensities.*—Full sunlight.

*Temperature.*—During day, grown in range of 18° C. to 40° C., and during evening, grow in range of −3° C. to 11° C.

*Fertilization.*—A balanced fertilizer with ratio NPK 1:0.3:1.1 (please note that the above values express ratio and not quantity, since quantity depends on the age of the plant).

*Growth regulators.*—None used, except in rooting of cuttings (IBA within range of 2000–3000 ppm).

*Pruning or trimming requirements.*—The size and shape of olive trees when mature essentially depends upon the kind of pruning and spacing used. The olive tree of 'GIULIA' was trained along a central leader creating a tree which is monocono and free palmetto in shape. When the trees are freely grown, the size and the shape assumed by the plants are typical of *Olea europaea L.* species.

Tree:

*Age.*—Observed trees were 10 years old.

*Vigor.*—Moderately weak vigor; early beginning production; high productivity.

*Habit and form.*—The olive tree of 'GIULIA' was trained along a central leader creating a tree which is monocono and free palmetto in shape.

*Crown density.*—Medium.

*Size at maturity.*—Height: Between about 3.5 meters and about 4.0 meters. Diameter of Canopy: About 2.6 meters.

*Attitude.*—Spreading.

*Abnormal leaves.*—Absent.

*Rooting attitude.*—High.

*Compatibility.*—Self-compatible.

*Trunk.*—Height (up to leaders): About 2.5 m. Diameter: About 12 cm. Texture: Bark color: Primarily greyed-green, RHS 194B, with yellow-white underbark, closest to RHS 11C. Trunk Lenticels: None.

*Branches.*—Number per tree: About 6. Branch size: The branch size (length and diameter) essentially depends upon the age of the branch observed. Length: The length of a one year old branch typically ranges from 15 cm to 25 cm. Diameter: The width of a one year old branch typically ranges from 4 mm to 7 mm. Crotch angle: The crotch angle of a one year old branch typically ranges from about 45 degrees to about 85 degrees, as measured from the longitudinal axes of the plant. Surface texture: Smooth. Pubescence: Fine hair or down generally present; color: greyed-green, RHS 191A. Color: Mature (after about one year old): Greyed-green, RHS 191B. New Growth: Light green, between RHS 130 C and RHS 13D. Internode length: Short, about 1.2 cm to 1.7 cm. Internode diameter: About 4 mm to 7 mm. Branch lenticels: None.

Leaves:

*Arrangement.*—The arrangement of the leaves is typical of *Olea europaea L.* species (two opposite leaves per each node).

*Lamina.*—General dimension/size: Medium. Longitudinal dimension: From 40 mm to 55 mm. Transversal dimension: From 13 mm to 15 mm. Axis ratio (length/width): Short and large (about 3.8).

*Longitudinal axis curvature of the blade.*—Flat.

*Twisting.*—Present.

*Overall shape.*—Elliptical-lanceolate.

*Apex shape.*—Rounded with slight swaging and twisting.

*Base shape.*—Rounded with slight swaging and twisting.

*Margin.*—Continuous.

*Texture.*—Upper surface: Glabrous and flat. Lower surface: Glabrous and flat.

*Pubescence.*—None.

*Leaf glossiness* (*both surfaces*).—Absent.

*Color* (*mature*).—Upper side: Dark-green, RHS 193A. Lower side: Greyed-green, RHS 195A.

*Color* (*immature*).—Upper side: Light green. Lower side: Greyed-green.

*Venation.*—Type: Not dense venation from central vein to the leaf edge, present but not evident, typical of olive species. Color: Light grey.

*Petiole.*—Length: About 3 m to 5 mm. Diameter: About 1.5 mm. Color: Greyed green, RHS 195C.

*Stipule.*—None.

Inflorescence:

*Blooming time.*—Late. The typical and observed flowering period for a culture in the Umbrian region (Central Italy) ranges from about May 10th to about June 30th.

*Blooming period.*—About 3 to 5 days

*Ripening time.*—Medium. The typical and observed ripening period for a culture in the Umbrian region (Central Italy) ranges from about November 10th to about December 10th.

*Fragrance.*—Dry fragrance, not characterizing since it is typical of olive species.

*Shape.*—Particulate spike-shaped.

*Structure.*—Long and compact.

*Ramification.*—Medium.

*Axillary flowers.*—Present.

*Number of flowers per inflorescence.*—About 16 to 20.

*Inflorescence size.*—Diameter: About 4 mm.

*Buds.*—Shape: Conical. Size: Medium. Length: About 2 mm. Width: About 1 mm. Color: Apex, Greyed-green, RHS 193B, and base, Greyed-green, RHS 193B.

*Petals.*—Typical of olive species. Number per flower: Four. Size: Length: About 3.0 mm to 4.0 mm. Width: About 2.0 mm to 3.0 mm. Color: Yellow-green, RHS 150D. Texture: Upper & under surfaces: Smooth.

*Sepals.*—Typical of olive species. Number per flower: Four. Size: Length: About 2.0 mm to 3.0 mm. Width: About 2.0 mm to 3.0 mm. Color: Yellow-green, RHS 141C. Texture: Upper and under surfaces: Smooth.

*Pedicel.*—Typical of olive species. Length: About 5.0 mm to 6.0 mm. Color: Yellow-green, RHS 150D. Texture: Upper and under surfaces: Smooth.

Reproductive organs: Reproductive organs (stamen and pistil), as well as the rest of the flower (petals and sepals) have the typical size, number, shape and color as species *Olea europaea L.* The percentage of ovary abortion is very low (less than about 5%) and the percentage of pollen viability is between about 95% and about 98% when the plant is at optimal nutrition.

Fruit (drupe): In the following description, Position A refers to the position in which the fruit shows its largest asymmetry. Position B can be reached from position A by turning 90 degrees along the longitudinal axes in a way that presents the most developed part of the fruit to the observer (according to UPOV rules).

*Maturity when described.*—Ripe for eating.

*Maturity period after full bloom.*—About 180 days after full bloom on November.

*Drupe detachment resistance.*—Medium (251–500 g).

*Overall shape.*—Elliptical.

*Apical shape.*—In Position A: Rounded. In Position B: Rounded.

*Base shape.*—In Position A: Truncated. In Position B: Rounded.

*Symmetry.*—In Position A: Slightly asymmetrical. In Position B: Symmetrical.

*Dimension.*—Medium, depending on the yield of the plant.

*Average weight.*—About 3.5 to 5.0 g.

*Longitudinal diameter.*—About 18 mm to 22.5 mm.

*Transversal diameter.*—About 12.5 mm to 15 mm.

*Transversal section shape.*—Circular.

*Colour.*—Dark violet, RHS 83A.

*Pigmentation.*—Medium.

*Mucron.*—Present.

*Pistil scar position.*—Central.

*Peduncular cavity.*—Shape: Circular. Width: Medium, about 1 mm. Depth: Deep, about 2 mm.

*Qualitative parameters.*—Oleic acid: Higher than 75%. Polyphenol content: Medium-high.

*Oil content* (*fresh matter based*).—About 18% to about 21%.

*Organoleptic characteristics of oil.*—High fruity: Intense with slightly bitter and pungent aftertaste. Typical characteristic of the oil: Particularly aromatic.

Stone (endocarp):

*Overall shape.*—In Position A: Elliptical. In Position B: Elliptical.

*Apex shape.*—In Position A: Rounded. In Position B: Rounded.

*Base shape.*—In Position A: Pointed. In Position B: Pointed.

*Symmetry.*—In Position A: Slightly asymmetrical. In Position B: Asymmetrical.

*Average weight.*—About 0.44 g to 0.47 g.

*Longitudinal diameter.*—About 14.5 mm to 16.5 mm.

*Transversal diameter.*—About 7.0 mm to 7.5 mm.

*Transversal section shape.*—Circular.

*Maximum transversal section position.*—Towards apex.

*Grooving.*—Weak.

*Groove distribution* (*at apex*).—Regular.

*Groove distribution* (*at base*).—Regular.

*Number of grooves at the base.*—About 7 to 10.

*Mucron.*—Present.

*Suture conspicuousness.*—Weak.

*Suture curvature.*—Present.

*Pulp/stone ratio.*—About 7.5 to 8.5.

*Pulp/stone detachment resistance.*—Easy.

Production:

*Production precocity.*—Precocious.

*Productivity.*—About 5,000 Kg/hectare to about 12,000 Kg/hectare in intensive plantations having 5'×3' spacing, depending on soil fertility and water availability.

*Production.*—Constant.

Resistance to abiotic factors:

*Cold.*—Medium-high. 'GIULIA' resists temperatures from as low as about −5° C. to about −7° C., during the winter when plants are in vegetative rest time.

*Water stress.*—Medium.

Resistance to parasites:

*Spilocaea oleagina.*—Medium.

*Pseudomonas syringae sb. savastanoi.*—Medium.

I claim:

1. A new and distinct *Olea europaea L.* olive tree variety named 'GIULIA', as illustrated and described herein.

* * * * *